United States Patent
Karam et al.

(10) Patent No.: US 11,318,086 B2
(45) Date of Patent: May 3, 2022

(54) COMPOSITIONS, METHODS, AND KITS FOR CLEANSING AND MOISIURIZING

(71) Applicants: Brandon Joseph Karam, San Antonio, TX (US); Jessica Karam Oley, San Antonio, TX (US)

(72) Inventors: Brandon Joseph Karam, San Antonio, TX (US); Jessica Karam Oley, San Antonio, TX (US)

(*) Notice: Subject to any disclaimer, the term of this patent is extended or adjusted under 35 U.S.C. 154(b) by 267 days.

(21) Appl. No.: 16/807,124

(22) Filed: Mar. 2, 2020

(65) Prior Publication Data

US 2020/0197293 A1 Jun. 25, 2020

Related U.S. Application Data

(63) Continuation of application No. 15/242,219, filed on Aug. 19, 2016, now Pat. No. 10,617,631.

(60) Provisional application No. 62/214,967, filed on Sep. 5, 2015.

(51) Int. Cl.
| | |
|---|---|
| *A61K 8/97* | (2017.01) |
| *A61K 8/34* | (2006.01) |
| *A61Q 19/00* | (2006.01) |
| *A61Q 19/10* | (2006.01) |
| *A61K 8/92* | (2006.01) |
| *A61K 8/9789* | (2017.01) |
| *A61K 8/9794* | (2017.01) |
| *A61K 8/67* | (2006.01) |

(52) U.S. Cl.
CPC .............. *A61K 8/922* (2013.01); *A61K 8/345* (2013.01); *A61K 8/678* (2013.01); *A61K 8/97* (2013.01); *A61K 8/9789* (2017.08); *A61K 8/9794* (2017.08); *A61Q 19/007* (2013.01); *A61Q 19/10* (2013.01); *A61K 2800/87* (2013.01)

(58) Field of Classification Search
CPC .... A61K 2800/87; A61K 8/345; A61K 8/678; A61K 8/97; A61Q 19/007; A61Q 19/10
See application file for complete search history.

(56) References Cited

U.S. PATENT DOCUMENTS 8,591,959 B1 * 11/2013 Kelly

FOREIGN PATENT DOCUMENTS

JP 59225111 A * 12/1984 ............. A61K 8/922

* cited by examiner

*Primary Examiner* — Aaron J Kosar

(57) ABSTRACT

Compositions, methods, and kits for cleansing, moisturizing, soothing, cooling, such as those, for example, that may be used to cleanse, moisturize, soothe, and cool the body or portions thereof.

20 Claims, No Drawings

COMPOSITIONS, METHODS, AND KITS FOR CLEANSING AND MOISIURIZING

CROSS-REFERENCE TO RELATED APPLICATIONS

This application claims the benefit of and priority to U.S. Non-Provisional patent application Ser. No. 15/242,219, filed Aug. 19, 2016, which claims the benefit of and priority to U.S. Provisional Patent Application Ser. No. 62/214,967, filed Sep. 5, 2015, the entirety of each of which is incorporated by reference.

BACKGROUND

1. Field of the Invention

The present invention relates generally to compositions, methods, and kits for cleansing, such as those, for example, that may be used to cleanse the body or portions thereof.

2. Description of Related Art

Examples of compositions for cleansing can be found, for example, at U.S. Pat. No. 8,158,567.

SUMMARY

This disclosure includes embodiments of compositions for cleansing, such as those comprising water; and a carrier oil; where the composition is configured to be applied to an anus of a subject. In some embodiments, the carrier oil is a first carrier oil, and the composition further comprises: a second carrier oil. In some embodiments, the first carrier oil comprises vegetable glycerin. In some embodiments, the second carrier oil comprises grapeseed oil. In some embodiments, the composition comprises from 10 to 20% by volume of the first carrier oil and from 10 to 20% by volume of the second carrier oil. In some embodiments, the compositions further comprise an essential oil. In some embodiments, the carrier oil comprises grapeseed oil, and the essential oil comprises peppermint oil. In some embodiments, the carrier oil comprises avocado oil, and the essential oil comprises geranium oil. In some embodiments, the essential oil comprises a first essential oil, the composition further comprising: a second essential oil. In some embodiments, the second essential oil comprises basil oil. In some embodiments, the composition comprises from 5 to 15% by volume of the carrier oil. In some embodiments, the composition comprises from 0 to 1% by volume of the first essential oil. In some embodiments, the composition comprises from 0 to 1% by volume of the first essential oil and from 0 to 1% by volume of the second essential oil. In some embodiments, the compositions further comprise an essential oil. In some embodiments, the first carrier oil comprises apricot oil, and the second carrier oil comprises coconut oil. In some embodiments, the composition comprises from 5 to 15% by volume of the first carrier oil and from 5 to 15% by volume of the second carrier oil. In some embodiments, the essential oil comprises Ylang Ylang oil. In some embodiments, the composition comprises from 0 to 1% by volume of the essential oil. In some embodiments, the compositions further comprise a cleansing agent. In some embodiments, the cleansing agent comprises witch hazel. In some embodiments, the composition comprises from 5 to 20% by volume of the cleansing agent. In some embodiments, the composition is disposed in a spray bottle such that the composition can be applied to an anus of a subject.

This disclosure further includes embodiments of methods for cleansing an anus of a subject, such as those comprising obtaining a composition comprising: water; and a carrier oil; and applying the composition to the anus of the subject. In some embodiments, the carrier oil is a first carrier oil, and the composition further comprises: a second carrier oil. In some embodiments, the first carrier oil comprises vegetable glycerin. In some embodiments, the second carrier oil comprises grapeseed oil. In some embodiments, the composition comprises from 10 to 20% by volume of the first carrier oil and from 10 to 20% by volume of the second carrier oil. In some embodiments, the composition further comprises an essential oil. In some embodiments, the carrier oil comprises grapeseed oil, and the essential oil comprises peppermint oil. In some embodiments, the carrier oil comprises avocado oil, and the essential oil comprises geranium oil. In some embodiments, the essential oil comprises a first essential oil, the composition further comprising: a second essential oil. In some embodiments, the second essential oil comprises basil oil. In some embodiments, the composition comprises from 5 to 15% by volume of the carrier oil. In some embodiments, the composition comprises from 0 to 1% by volume of the first essential oil. In some embodiments, the composition comprises from 0 to 1% by volume of the first essential oil and from 0 to 1% by volume of the second essential oil. In some embodiments, the composition further comprises an essential oil. In some embodiments, the first carrier oil comprises apricot oil, and the second carrier oil comprises coconut oil. In some embodiments, the composition comprises from 5 to 15% by volume of the first carrier oil and from 5 to 15% by volume of the second carrier oil. In some embodiments, the essential oil comprises Ylang Ylang oil. In some embodiments, the composition comprises from 0 to 1% by volume of the essential oil. In some embodiments, the composition further comprises a cleansing agent. In some embodiments, the cleansing agent comprises witch hazel. In some embodiments, the composition comprises from 5 to 20% by volume of the cleansing agent. In some embodiments, applying the composition to the anus of the subject comprises: spraying the composition from a spray bottle onto the anus of the subject; and wiping the composition from the anus of the subject. In some embodiments, applying the composition to the anus of the subject comprises: spraying the composition from a spray bottle onto tissue paper; and wiping the tissue paper on the anus of the subject. In some embodiments, obtaining a composition comprises: pouring the composition from a container into a spray bottle.

Some compositions of this disclosure comprise: water; oil; a preservative; an emulsifier; where the composition comprises at least 3% oil by volume; where the composition is a substantially stable emulsion; and where the composition is configured to at least one of cleanse and moisturize the skin of a subject. In some embodiments, the composition comprises at least 5% oil by volume. In some embodiments, the composition comprises at least 10% oil by volume. In some embodiments, the composition comprises from 10% to 30% oil by volume. In some embodiments, the composition comprises a viscosity suitable to enable the composition to be atomized by a sprayer at room temperature. In some embodiments, the composition comprises a viscosity suitable to enable the composition to be atomized by a sprayer at room temperature without creating a blockage in the sprayer that substantially prevents exit of the composition. In some embodiments, the composition is emulsified by a hot process. In some embodiments, the composition is emulsified by a cold process. In some embodiments, the oil comprises a first carrier oil and a second carrier oil. In some embodiments, each of the ingredients in the composition is naturally occurring or naturally derived.

Some compositions of this disclosure comprise: water at about 55-80% by volume; at least one carrier oil at about 5-15% by volume; at least one essential oil at about 0.2-0.6% by volume; at least one cleansing agent at about 5-15% by volume; at least one preservative at about 0.5-2% by volume; at least one emulsifier at about 5-15% by volume; where the composition is a substantially stable emulsion; where the composition is configured to cleanse the skin of a subject; where the composition is substantially liquid such that it can be atomized by a spraying device without creating a blockage in the spraying device that substantially prevents exit of the composition; where each ingredient in the composition is naturally occurring or naturally derived; and where the composition is a rinse-free composition. In some embodiments, the composition comprises less than or equal to about 8% of the at least one emulsifier by volume. In some embodiments, a viscosity of the composition comprises less than or equal to approximately 20 millipascal-seconds at room temperature. In some embodiments, the substantially stable emulsion occurs at least in part by heating at least a portion of the composition during mixing. In some embodiments, the composition comprises greater than or equal to about 10% of the at least one carrier oil.

Some methods of the present disclosure comprise preparing a composition comprising: water at about 55-80% by volume; at least one carrier oil at about 5-15% by volume; at least one cleansing agent at about 5-15% by volume; at least one emulsifier at about 5-15% by volume; where the composition is a substantially stable emulsion; where the composition is configured to cleanse the skin of a subject; where the composition is a rinse-free composition; disposing the composition in a spray bottle; spraying the composition on toilet paper; applying the composition to the anus of a subject; leaving at least some of the composition on the anus of the subject. In some embodiments, each ingredient in the composition is naturally occurring or naturally derived. In some embodiments, the composition is scented, the method further comprising spraying the composition into the air to freshen the air.

Some compositions of this disclosure comprise oil at about 5-15% by volume; at least one cleansing agent at 10% or greater by volume; at least one emulsifier at 15% or less by volume; where the composition is a substantially stable emulsion; where the composition is configured to cleanse the skin of a subject; where the at least one emulsifier is at a percent by volume sufficiently low to enable the composition to be atomized by a spraying device without creating a blockage in the spraying device that substantially prevents exit of the composition; and where the composition is a rinse-free composition. In some embodiments, each ingredient in the composition is naturally occurring or naturally derived. In some embodiments, the composition is organic. In some embodiments, the compositions further comprise water at about 55-80% by volume; and at least one preservative; where the at least one preservative is naturally occurring. In some embodiments, the compositions further comprise water at about 55-80% by volume; and at least one preservative; where the at least one preservative is naturally derived. In some embodiments, the viscosity of the composition is less than or equal to about 100 millipascal-seconds at room temperature. In some embodiments, the composition comprises the at least one cleansing agent at about 50% or greater. In some embodiments, the oil at about 5-15% by volume comprises: a first carrier oil at about 3-4% by volume; a second carrier oil at about 3-4% by volume; and at least one essential oil at about 0.3-2% by volume. In some embodiments, the at least one essential oil is scented, where the at least one essential oil comprises sufficient antimicrobial properties to preserve the composition, and where each ingredient in the composition is naturally occurring or naturally derived. In some embodiments, the composition comprises the at least one emulsifier at about 8% or less by volume. In some embodiments, the composition comprises a pH of about 4-5. In some embodiments, the emulsion is created by a cold process.

This disclosure further includes embodiments of kits, such as those for cleansing the body or portions thereof, such as the anus, where the kits comprise one or more of the compositions of the present disclosure and one or more of a spray bottle and a substrate/removal material (e.g., dry tissue paper).

The terms "a" and "an" are defined as one or more unless this disclosure explicitly requires otherwise.

The term "substantially" is defined as largely but not necessarily wholly what is specified (and includes what is specified; e.g., substantially 90 degrees includes 90 degrees), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a composition, or a component of a composition, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps.

Terms such as "first" and "second" are used only to differentiate ingredients or features, and not to limit the different ingredients or features to a particular order or to a particular quantity.

The term "carrier oil," which include other terms, such as "vegetable oils," "fixed oils," and "base oils," is used to refer to oils that are extracted from a plant, such as by cold pressing or maceration, or other fluid produced from such oils, in a manner that results in a less concentrated, stable (i.e., having a tendency to not evaporate or to evaporate slowly at room temperature) oil.

The term "essential oil" is used to refer to oils that are extracted from a plant, such as by distillation (e.g., steam distillation), centrifugal, solvent extraction, and the like, or other fluid produced from such oils, in a manner that results in a highly concentrated and often volatile (i.e., having a tendency to evaporate at room temperature) oil. A carrier oil and an essential oil can be derived from the same type of plant, though each oil may have different characteristics. At least some of the oils disclosed herein can comprise a carrier oil or an essential oil depending on the manner in which they are derived, the concentration of the oil, the evaporation rate of the oil, and other properties.

The terms "rinse free" or "leave on" are used to refer to a composition that is configured to remain on the skin of a subject without causing redness, irritation, or other negative or unintended effects that would otherwise occur if a composition is configured such that it should be removed from the skin.

The term "organic" means an organic product as defined by the National Organic Program (NOP) as overseen by the U.S. Department of Agriculture (USDA).

Any embodiment of any of the present compositions and methods can consist of or consist essentially of—rather than comprise/include/contain/have—any of the described elements and/or features. Thus, in any of the claims, the term "consisting of" or "consisting essentially of" can be substituted for any of the open-ended linking verbs recited above in order to change the scope of a given claim from what it would otherwise be using the open-ended linking verb.

The feature or features of one embodiment may be applied to other embodiments, even though not described unless expressly prohibited by this disclosure or the nature of the embodiments.

Details associated with the embodiments described above and others are presented below.

DESCRIPTION OF ILLUSTRATIVE EMBODIMENTS

According to one embodiment, the compositions of the present disclosure comprise water (e.g., tap water, purified water, distilled water, etc.), and a carrier oil (e.g., as described throughout this disclosure), where the composition is configured to be applied to an anus of a subject. In some embodiments, the composition is disposed in a container that is configured to dispense the composition, such as, for example, a spray bottle, an autosprayer, and the like. In some embodiments, the composition can be applied directly to the anus of a subject, such as by spraying the composition from a spray bottle toward the anus of a subject, and the composition can be removed from the anus of a subject by wiping or rubbing the composition with a removal material (e.g., toilet tissue/tissue paper, wet wipes, towels (e.g., paper, cloth, etc.), towelettes, and the like). In other embodiments, the composition can be applied indirectly to the anus of a subject, such as by applying (e.g., spraying) the composition to a substrate (e.g., toilet tissue/tissue paper, wet wipes, towels (e.g., paper, cloth, etc.), towelettes, and the like) and applying the composition to the anus with the substrate. In such an embodiment, the composition can be removed from the anus of a subject by wiping or rubbing the composition with the substrate, or with an independent removal material, or the composition can be configured to be leave-on or rinse-free. The composition can be configured to offer cleansing, moisturizing, cooling, soothing, and other characteristics, as described below.

In some embodiments, the compositions comprise water, such as distilled water, purified water, and other forms of water. In some embodiments, the present compositions are oil in water emulsions, in other embodiments, the compositions are water in oil emulsions, and in still other embodiments, the compositions comprise water and oil that are not emulsified in a shake and spray formulation. In some embodiments, the compositions comprise less than 50% water by volume (e.g., 40-50% water by volume, 30-40% water by volume, 20-30% water by volume, 10-20% water by volume, less than 10% water by volume, or any amount therebetween). In other embodiments, the compositions comprise greater than 50% water by volume (e.g., 60% water by volume, 70% water by volume, 80% water by volume, 90% water by volume, more than 90% water by volume, or any amount therebetween. For example, some compositions comprise 55-80% water by volume, some compositions comprise 55-65% water by volume, some compositions comprise 65-75% water by volume, and some embodiments comprise 75-85% water by volume. In some embodiments, the compositions do not comprise water and comprise mixtures of other ingredients in this disclosure.

In some embodiments, the present compositions comprise one or more oils, and in some instances at a high oil content by volume to, for example, provide a moisturizing and/or soothing consistency. For example, in some embodiments the present compositions can comprise one or more oils (e.g., carrier oils) for a total of at least 2% oil by volume, at least 3% oil by volume, at least 5% oil by volume, at least 8% oil by volume, at least 10% oil by volume, at least 12% oil by volume, at least 15% oil by volume, at least 18% oil by volume, at least 20% oil by volume, or more. For example, some embodiments comprise from 10% to 30% oil by volume, some embodiments comprise from 5%-15% oil by volume, some embodiments comprise 5%-10% oil by volume, some embodiments comprise 10%-15% oil by volume, and some embodiments comprise 15%-20% oil by volume. As another example, in some embodiments, the compositions can comprise a first oil, such as a carrier oil, from at least 2% (e.g., 3% by volume, 4% by volume, 5% by volume, 6% by volume, 7% by volume, 8% by volume, 9% by volume, 10% by volume, or more). In other embodiments, the compositions can further comprise a second oil, such as carrier oil, from at least 2% by volume (e.g., 3% by volume, 4% by volume, 5% by volume, 6% by volume, 7% by volume, 8% by volume, 9% by volume, 10% by volume, or more). In still other embodiments, the compositions can further comprise a third oil, such as a carrier oil, from at least 2% by volume (e.g., 3% by volume, 4% by volume, 5% by volume, 6% by volume, 7% by volume, 8% by volume, 9% by volume, 10% by volume, or more). In other embodiments, the composition can comprise a fourth, fifth, and sixth oil at similar percentages by volume. In other embodiments, the one or more oils can comprise less than 2% by volume, and the sum of the percentages by volume of each carrier oil is greater than 2% by volume. In some embodiments, some or all of the one or more oils are naturally occurring, naturally derived, or organic.

In some embodiments, the compositions comprise more than one carrier oil, such as a first carrier oil, a second carrier oil, a third carrier oil, a fourth carrier oil, or more. The one or more carrier oils can be present in various amounts. For example, the composition can comprise from 5 to 20% by volume of a first carrier oil, from 5 to 20% by volume of a second carrier oil, from 5 to 20% by volume of a third carrier oil, from 5 to 20% by volume of a fourth carrier oil, and the like. However, depending on the desired characteristics of a given composition, the composition can comprise greater than 20% by volume of one or more carrier oils (e.g., 25%, 30%, 35%, 40%, or more), or less than 5% by volume of one or more carrier oils (e.g., 4%, 3%, 2%, 1%, or less).

In one embodiment, the composition comprises vegetable glycerin as a carrier oil. For example, the composition can comprise from 5 to 20% by volume (which will vary in quantity depending, for example, on the size of the container, the volume of composition, etc.) of vegetable glycerin. Vegetable glycerin is derived from vegetable oil, and it comprises moisturizing, cleansing, softening, hypoallergenic, and lubricating characteristics. It further comprises favorable water solubility characteristics.

In one embodiment, the composition comprises grapeseed oil as a carrier oil. For example, the composition can comprise from 5 to 20% by volume (which will vary in quantity depending, for example, on the size of the container, the volume of composition, etc.) of grapeseed oil. Grapeseed oil is a light oil that comprises moisturizing, astringent, antimicrobial, and antiseptic characteristics, at least some of which can, for example, assist with skin repair and/or alleviate chapped, inflamed, dry, or itchy skin.

In one embodiment, the composition comprises apricot oil as a carrier oil. For example, the composition can comprise from 5 to 20% by volume (which will vary in quantity depending, for example, on the size of the container, the volume of composition, etc.) of apricot oil. Apricot oil is a light oil that comprises fatty acids, Vitamin A, and Vitamin E. Apricot oil further comprises moisturizing and restorative characteristics.

In one embodiment, the composition comprises avocado oil as a carrier oil. For example, the composition can comprise from 5 to 20% by volume (which will vary in quantity depending, for example, on the size of the container, the volume of composition, etc.) of avocado oil. Avocado oil comprises collagen-supporting amino acids, proteins, and antioxidants, such as Vitamin A, Vitamin D, and Vitamin E. oil is a light oil that comprises fatty acids, Vitamin A, and Vitamin E. Apricot oil further comprises moisturizing and restorative characteristics. Avocado oil further comprises moisturizing characteristics, which can, for example assist in relieving irritated and itchy skin.

In one embodiment, the composition comprises coconut oil as a carrier oil. For example, the composition can comprise from 5 to 20% by volume (which will vary in quantity depending, for example, on the size of the container, the volume of composition, etc.) of coconut oil. In some embodiments, the coconut oil can be fractionated coconut oil is created at least in part by removing long-chain triglycerides from coconut oil, leaving medium-chain triglycerides and raising concentrations of Capric and Caprylic fatty acids. Coconut oil, including fractionated coconut oil comprises moisturizing, antimicrobial, antioxidant, and disinfecting characteristics.

As will be described in more detail below, a composition can comprise a number of other carrier oils depending, for example, on the desired characteristics of a composition.

In some embodiments, the compositions comprise one or more essential oils, such as one essential oil, two essential oils, three essential oils, four essential oils, or more. The one or more essential oils can be present in various amounts. For example, the composition can comprise from 0 to 1% by volume of a first essential oil, from 0 to 1% by volume of a second essential oil, from 0 to 1% by volume of a third essential oil, from 0 to 1% by volume of a fourth essential oil, and the like. However, depending on the desired characteristics of a given composition, the composition can comprise greater than 1% by volume of one or more essential oils (e.g., 1.1%, 1.2%, 1.3%, 1.4%, 1.5%, or more). For example, in some embodiments, the compositions can comprise one or more essential oils at about 0.2-0.6% by volume. As another example, some embodiments can comprise at least one essential oil at about 0.3-2% by volume. In some embodiments, some or all of the one or more essential oils are naturally occurring, naturally derived, or organic. In some embodiments, the one or more essential oils is scented.

In some embodiments, the one or more essential oils comprises sufficient anti-microbial properties to preserve the composition.

In one embodiment, the composition comprises peppermint oil as an essential oil. For example, the composition can comprise from 0 to 1% by volume (which will vary in quantity depending, for example, on the size of the container, the volume of composition, etc.) of peppermint oil. Peppermint oil comprises anti-inflammatory, anti-fungal, and cooling characteristics, at least some of which can assist in reducing swelling, relieving pain, and eliminating inflammation.

In one embodiment, the composition comprises geranium oil as an essential oil. For example, the composition can comprise from 0 to 1% by volume (which will vary in quantity depending, for example, on the size of the container, the volume of composition, etc.) of geranium oil. Geranium oil comprises anti-inflammatory, anti-irritation, anti-bacterial, and regenerative characteristics.

In one embodiment, the composition comprises basil oil as an essential oil. For example, the composition can comprise from 0 to 1% by volume (which will vary in quantity depending, for example, on the size of the container, the volume of composition, etc.) of basil oil. Basil oil comprises Vitamin A and further comprises antispasmodic, antibacterial, and anti-inflammatory, and analgesic characteristics.

In one embodiment, the composition comprises ylang ylang oil as an essential oil. For example, the composition can comprise from 0 to 1% by volume (which will vary in quantity depending, for example, on the size of the container, the volume of composition, etc.) of ylang ylang oil. Ylang ylang oil can assist in maintaining moisture and oil balance of skin, as well as maintaining skin hydration and smoothness.

As will be described in more detail below, a composition can comprise a number of other essential oils depending, for example, on the desired characteristics of a composition.

In some embodiments, the compositions comprise one or more cleansing agents, such as one cleansing agent, two cleansing agents, three cleansing agents, four cleansing agents, or more. The one or more cleansing agents can be present in various amounts. For example, the composition can comprise from 5 to 20% by volume of a first cleansing agent, from 5 to 20% by volume of a second cleansing agent, from 5 to 20% by volume of a third cleansing agent, from 5 to 20% by volume of a fourth cleansing agent, and the like. However, depending on the desired characteristics of a given composition, the composition can comprise greater than 20% by volume of one or more cleansing agents (e.g., 25%, 30%, 35%, 40%, or more), or less than 5% by volume of one or more cleansing agents (e.g., 4%, 3%, 2%, 1%, or less).

In some embodiments, the present compositions comprise one or more cleansing agents, and in some instances a high cleansing agent content by volume to, for example, cleanse the skin of the subject (e.g., by removing and/or preventing at least some microbes, bacteria, and the like). For example, in some embodiments the present compositions can comprise one or more cleansing agents for a total of at least 3% cleansing agent by volume, at least 5% cleansing agent by volume, at least 8% cleansing agent by volume, at least 10% cleansing agent by volume, at least 12% cleansing agent by volume, at least 15% cleansing agent by volume, at least 18% cleansing agent by volume, at least 20% cleansing agent by volume, or more. In some embodiments, the one or more cleansing agents comprise at least 50% cleansing agent by volume or more, such as 55% cleansing agent by volume, 60% cleansing agent by volume, 65% cleansing agent by volume, 70% cleansing agent by volume, 75% cleansing agent by volume, 80% cleansing agent by volume, 85% cleansing agent by volume, 90% cleansing agent by volume, or more. For example, some embodiments comprise from 10% to 30% cleansing agent by volume, some embodiments comprise from 5%-15% cleansing agent by volume, some embodiments comprise 5%-10% cleansing agent by volume, some embodiments comprise 10%-15% cleansing agent by volume, and some embodiments comprise 15%-20% cleansing agent by volume. As another example, in some embodiments, the compositions can comprise a first cleansing agent from at least 3% by volume (e.g., 3% by volume, 4% by volume, 5% by volume, 6% by volume, 7% by volume, 8% by volume, 9% by volume, 10% by volume, or more). In other embodiments, the compositions can further comprise a second cleansing agent from at least 3% by volume (e.g., 3% by volume, 4% by volume, 5% by volume, 6% by volume, 7% by volume, 8% by volume, 9% by volume, 10% by volume, or more). In still other embodiments, the compositions can further comprise a third cleansing agent from at least 3% by volume (e.g., 3% by volume, 4% by volume, 5% by volume, 6% by volume, 7% by volume, 8% by volume, 9% by volume, 10% by volume, or more). In other embodiments, the composition can comprise a fourth, fifth, and sixth cleansing agent at similar percentages by volume. In other embodiments, the one or more cleansing agents can comprise less than 3% by volume, and the sum of the percentages by volume of each cleansing agent is greater than 3% by volume. In some embodiments, some or all of the one or more cleansing agents are naturally occurring, naturally derived, or organic.

In one embodiment, the composition comprises witch hazel as a cleansing agent. For example, the composition can comprise from 5 to 20% by volume (which will vary in quantity depending, for example, on the size of the container, the volume of composition, etc.) of witch hazel. In some embodiments, the composition comprises witch hazel distillate, which comprises benzoic acid (e.g., from 0 to 1% (e.g., 0.15%)) as a preserving agent. In other embodiments, witch hazel can comprise alcohol as a preserving agent; and in still other embodiments, witch hazel does not independently comprise a preserving agent. Witch hazel comprises cleansing, astringent, soothing, anti-irritation, and anti-inflammation properties, at least some of which assist, for example, in relieving hemorrhoids.

As will be described in more detail below, a composition can comprise a number of other cleansing agents depending, for example, on the desired characteristics of a composition.

Other examples of carrier oils and essential oils that can be used in the present compositions, either alone or in combination with each other or other ingredients in this disclosure, include Aloe Vera oil, Almond oil, Sweet Almond oil, Apricot Kernel Oil, Bergamot oil, Cardamom oil, Castor oil, Carrot seed oil, Cassia oil, Cedar (e.g., Western Red) oil, Cedarwood oil, Celery seed oil, Chamomile oil (e.g., German, Roman, etc.), Cinnamon Bark oil, Cistus citronella oil, Citrus hysteix oil, Clary Sage oil, Clove oil, Copaiba oil, Coriander oil, Cumin oil, Cypress oil (e.g., Blue), Davana oil, Dill oil, Dorado Azulejo oil, Elemi oil, Eucalyptus oil (e.g., Blue, Citriodora. Dives, Globus, Lemon, Polybractea, Radiata, etc.), Fennel oil, Flax oil, Douglas Fir oil, White Fir oil, Frankincense oil, Ginger oil, Goldenrod oil, Grapefruit oil, Helichrysum oil, Hemp oil, Hyssop oil, Jasmine oil, Jojoba oil, Juniper oil, Laurus Nobilis oil, Lavandin oil, Lavender oil, Ledum oil, Lemon oil, Lemongrass oil, Lime oil, Mandarin oil, Manuka oil, Marjoram oil, Melaleuca oil (e.g., Alternifolia, Cajeput, Ericifolia, Quinquenervia), Melissa oil, Mountain Savory oil, Menthol oil, Mugwort oil, Myrrh oil, Myrtle oil, Neem oil, Neroli oil, Nutmeg oil, Ocotea oil, Olive oil, Orange oil, Oregano oil, Palmarosa oil, Palo Santo oil, Patchouli oil, Black Pepper oil, Petitgrain oil, Pine oil, Primrose oil, Ravintsara oil, Rose oil, Rosemary oil, Rosewood oil, Sage oil (e.g., Spanish), Sandalwood oil, Spearmint oil, Spikenard oil, Spruce oil, Sweet Basil Oil, Tangerine oil, Tansy oil (e.g., Blue, Idaho, etc.), Tarragon oil, Tea Tree oil, Thyme oil, Tsuga oil, Valerian oil, Vetiver oil, White Lotus oil, Wintergreen oil, and Yarrow oil.

Other examples of cleansing agents that can be used in the present compositions, either alone or in combination with each other or other ingredients in this disclosure, include soaps (e.g., Castile soap), alcohol, vinegar, baking soda, lemon juice, witch hazel, Sodium Lauryl Glucose Carboxylate, Lauryl Glucoside, and the like. As described above, at least some of the above-described oils contain cleansing properties and can be considered cleansing agents.

The present compositions can also comprise emulsifying agents, surfactant agents, solubilizers, and/or stabilizing agents, collectively referred to as emulsifiers herein, which, for example, discourage separation of ingredients in the compositions, stabilize the compositions, and/or increase storage life of the compositions. In some embodiments, the present compositions comprise one or more emulsifiers, and in some instances a high emulsifier content by volume to, for example, enable a stable emulsion in a composition that comprises a variety of ingredients, and in some instances, a composition that comprises a high oil content (e.g., by removing and/or preventing at least some microbes, bacteria, and the like). For example, in some embodiments the present compositions can comprise one or more emulsifiers for a total of at least 3% emulsifier by volume, at least 5% emulsifier by volume, at least 7% emulsifier by volume, at least 10% emulsifier by volume, at least 12% emulsifier by volume, at least 15% emulsifier by volume, at least 18% emulsifier by volume, at least 20% emulsifier by volume, or more. For example, some embodiments comprise from 10% to 20% emulsifier by volume, some embodiments comprise from 5%-15% emulsifier by volume, some embodiments comprise 5%-10% emulsifier by volume, some embodiments comprise 10%-15% emulsifier by volume, and some embodiments comprise 15%-20% emulsifier by volume. As another example, in some embodiments, the compositions can comprise a first emulsifier from at least 3% by volume (e.g., 3% by volume, 4% by volume, 5% by volume, 6% by volume, 7% by volume, 8% by volume, 9% by volume, 10% by volume, or more). In other embodiments, the compositions can further comprise a second emulsifier from at least 3% by volume (e.g., 3% by volume, 4% by volume, 5% by volume, 6% by volume, 7% by volume, 8% by volume, 9% by volume, 10% by volume, or more). In still other embodiments, the compositions can further comprise a third emulsifier from at least 3% by volume (e.g., 3% by volume, 4% by volume, 5% by volume, 6% by volume, 7% by volume, 8% by volume, 9% by volume, 10% by volume, or more). In some embodiments, the one or more emulsifiers is present at 15% by volume or less, at 10% by volume or less, at 8% by volume or less, at 7% by volume or less, at 6% by volume or less, or at 6% by volume or less. In other embodiments, the composition can comprise a fourth, fifth, and sixth emulsifier at similar percentages by volume. In other embodiments, the one or more emulsifiers can comprise less than 3% by volume, and the sum of the percentages by volume of each emulsifier is greater than 3% by volume. In some embodiments, some or all of the one or more emulsifiers are naturally occurring, naturally derived, or organic.

The presence of an emulsifier in the present compositions is intended to create a substantially stable emulsion, and, at least in some instances, a substantially stable emulsion in a high oil content composition, and, in additional instances, with naturally occurring, naturally derived, or organic ingredients. In some embodiments, the composition comprises the one or more emulsifiers and/or the one or more oils at a percentage that results in a composition viscosity suitable to enable the composition to be atomized by a sprayer at room temperature (e.g., an emulsion that is not so thick that it, immediately or over time, creates a blockage in the sprayer that substantially prevents exit of the composition, or an emulsion that is so thin that it does not provide the moisturizing, soothing, cleansing, and other properties described throughout this disclosure). In some embodiments, the specific gravity of the compositions at room temperature is substantially equal to 1, where water is a reference substance. For example, in some embodiments, the specific gravity of the compositions at room temperature is approximately 0.95 to 1, and in other embodiments, the specific gravity of the compositions at room temperature is approximately 1 to 1.05. In some embodiments, the specific gravity of the compositions at room temperature is less than 0.95 (e.g., 0.9, 0.85, 0.8, 0.75, or less), and in other embodiments, the specific gravity of the compositions at room temperature is greater than 1.05 (e.g., 1.1, 1.15, 1.2, 1.25, or more). For example, in some embodiments, the compositions comprise a viscosity of less than or equal to approximately 20 millipascal-seconds at room temperature (e.g., from 15 and 20 millipascal-seconds at room temperature, from 10-15 millipascal-seconds at room temperature, from 5-10 millipascal-seconds at room temperature, from 1-5 millipascal-seconds at room temperature, etc.). In some embodiments, the composition is emulsified at least in part by a hot process, such as by heating at least a portion of the composition during mixing. In other embodiments, the composition is emulsified by a cold process. In some embodiments, the emulsified composition comprises a viscosity that is different from and/or lower than the viscosity of a lotion. In some embodiments, the emulsified composition comprises a viscosity that is different from and/or lower than the viscosity of a gel. In some embodiments, the emulsified composition comprises a viscosity that is different from and/or lower than a foam. In some embodiments, the ingredients of the compositions do not cause the composition to foam (e.g., when shaken or disturbed).

Examples of emulsifying agents that can be used in the present compositions, either alone or in combination with each other or other ingredients in this disclosure, include palm stearic cetearyl alcohol, polysorbate 60, sorbitan monostearate, beeswax, borax, Alkyldimethylamine oxide, Ammonium cocoyl isethionate, Ammonium Steratearachidonic acid, Arachidyl glucoside, Brassicyl Isoleucinate Esylate and Brassica Alcohol, Brassicyl Isoleucinate Eslate and Brassica Glycerides, Butyl sterate, C 12-20 Alkyl Glucoside, C14-22 alcohols, Carnitine, Cetearyl Alcohol, Cetearyl Glucoside, Cetyl Alcohol, Cetyl Esters, Cocamidopropyl Betaine, Cocomidopropyl Hydroxysultaine, Coco-Glucoside, Decyl Glucoside, Decyl Polyglucose, Disodium Coco-Glucoside Citrate, Disodium Coco-Glucoside Sulfosuccinate, Disodium Cocoamphodiacetate, Disodium Cocoamphodipropionate, Disodium Lauroamphodiacetate, Disodium Soyamphodiacetate, Disodium Wheatgermamphodiacetate, Emulsifying wax nf, Glyceryl Caprylate, Glyceryl Tricaprylate/Tricaprate, Glyceryl Citrate, Glyceryl Cocoate, Glyceryl Dilaurate, Glyceryl Monolaurate, Monocaprylate, Glyceryl Monostearate, Glyceryl Oleate, Glyceryl Stearate, Glyceryl Stearate SE, Glycol Stearate, Glyceryl Sterate Citrate, Hydrogenated Lecithin, Hydrogenated Palm Glyceride, Lauroamphoglycinate, Lithium Stearate, Lecithin (Liquid), Octyl Palmitate, Octyl Sterate, Octyldodecyl Stearoyl Stearate, Polyglyceryl-3 Caprate, Polyglyceryl-3 Ricineoleate, Polysorbate 20, Polysorbate 80, Potassium Cocoate, Potassium Oleate, Potassium Olivoyl PCS, Potassium Stearate, Safflower Oleosomes, Sodium Caproyl Lactylate, Sodium Carboxymethyl Lauryl Glucoside, Sodium Coco-Glucoside Tartrate, Sodium Cocobutteramphoacetate, Sodium Cocoamphoacetate, Sodium Cocoate, Sodium Cocopolyglucose tartrate, Sodium Cocoyl Apple Amino Acids, Sodium Cocoyl Sulfoacetate, Sodium Kernaelate, Sodium Lauroamphoacetate, Sodium Lauroyl Glutamate, Sodium Lauroyl Lactylate, Sodium Lauroyl Methyl Isethionate, Sodium Lauroyl Sarcosinate, Sodium Lauryl Glucose Carboxylate, Sodium Laurylglucosides Hydroxypropylsulfonate, Sodium Methyl Cocoyl Taurate, Sodium Myrisate, Sodium Myristoyl Glutamate, Sodium Myristoyl Sarcosinate, Sodium Oleoyl Sarcosinate, Sodium Olivate, Sodium Palm Kernelate, Sodium Palmate, Sodium Laurate, Sorbitan Olivate, Sorbitan Sesquicaprylate, Sorbitan Sesquioleate, Sorbitan Stearate, Sucrose Cocoate, Surcrose Distearate, Sucros Palmitate, Stearic Acid, Soy Lecithin (organic and non-organic), Polyglyceryl-2 Stearate (and) Glyceryl Stearate (and) Stearyl Alcohol (PolyAquol™ 2W), Polyglyceryl-2 Oleate, Polyhydroxystearic Acid, Polyglyceryl-2 Stearate (PolyAquol™ OS2), Octyldodecyl Oleate (and) Octyldodecyl Stearoyl Stearate (and) Polyhydroxystearic Acid (and) Octyldodecanol (Innollient™ LO) and combinations thereof. Emulsifying agents can be included in the present compositions from 0 to 10% by volume, depending in part on the amount of oil in a composition, among other things. In other embodiments, emulsifiers can be included in greater than 10% by volume, such as at 12% by volume, 15% by volume, 18% by volume, 20% by volume, or more.

The present compositions can also comprise antioxidants to, for example, extend the life of the compositions and/or prevent degradation of one or more ingredients in the compositions. Examples of antioxidants that can be used in the present compositions, either alone or in combination with each other or other ingredients in this disclosure, include Vitamin E Mixed Tocopherol (e.g., naturally derived from a non-GMO base or synthetic), Grapefruit seed extract, Neem Oil, Alpha tocopherol, and Rosemary oil extract.

The present compositions can also comprise preservatives, antimicrobials, and/or antibacterials to increase storage life of the compositions and/or to remove, reduce, and/or prevent microbial or bacteria growth. In some embodiments, the compositions comprise one or more preservatives, such as one preservative, two preservatives, three preservatives, four preservatives, or more. The one or more preservatives can be present in various amounts. For example, the composition can comprise from 0 to 1% by volume of a first preservative, from 0 to 1% by volume of a second preservative, from 0 to 1% by volume of a third preservative, from 0 to 1% by volume of a fourth preservative, and the like. In some embodiments, the compositions comprise greater than 1% by volume of one or more preservatives (e.g., 1.1%, 1.2%, 1.3%, 1.4%, 1.5%, 1.6%, 1.7%, 1.8%, 1.9%, 2%, 2.5%, 3%, 3.5%, 4% or more). For example, in some embodiments, the compositions can comprise one or more preservatives at about 0.5-2% by volume. As another example, some embodiments can comprise at least one preservative at about 0.5-1.5% by volume. In some embodiments, some or all of the one or more preservatives are naturally occurring, naturally derived, or organic. In some embodiments, some or all of the one or more preservatives are essential oils.

Examples of preservatives include Rosemary Oil Extract, Aspen Bark Extract, Blackcurrant Extract, Elderberry Extract, Grapefruit Seed Extract, Lactobacillus Ferment, LactoCoconut Extract, LiquaPar Oil, Vitamin E Mixed Tocopherol (e.g., naturally derived from a non-GMO base or synthetic), Neem Oil, Sweet Orange Oil, Tea Tree Essential Oil, Citric Acid, Alpha tocopherol, Caprylyl Glycol, Caprylic Acid, Citrus Aurantium, Cymbopogon Citratus, Helinathus Annuus (Linatural™ Co-NLP-1), Citrus Aurantium, Cymbopogon Citratus, Sesamum Indicum (Linatural™ NLP-0), Caprylhydroxamic acid, Caprylic Acid, Caprlohydroxamic Acid, Capryloyl Glycerin, Capryloyl Glycine, Dehydroacetic acid, Denatured alcohol (SD 38 & 40), Ethyl Alcohol, Ethylhexyl Diglycerin, Ethylhexyl Glycerin, Ferulic Acid, Gluconi Acid, Glucose Oxidase, Glyceryl Laurate, Glyceryl Undecylenate, Phenethyl Alcohol, 1.3 Propanediol, Ethylhexyl Glycerin, Benzoic Acid (Linatural™ MBS-1), Phenethyl Alcohol, Glycerin, Benzoic Acid (Linatural™ PA Plus), Pentylene Glycol, Glycerin, Benzoic Acid (Linatural™ PG Plus), Pentylene Glycol, Ethylhexyl Glycerin, Glycerin, Benzoic Acid (Linatural™ PG-2), Propanediol, Benzyl alcohol, Pentylene Glycol (Linatural™ Ultra-1), Propanediol, Pentylene Glycol, Phenethyl Alcohol (Linatural™ Ultra-3), Polylysine, Potassium Sorbate, SD-alcohol 30, SD-alcohol 40, Sodium Levulinate, Sodium Sulfite, Sorbic Acid, Suprapein™, and combinations thereof.

The present compositions can also comprise one or more skin conditioning agents, emollients, and/or lubricants. Examples of skin conditioning agents, emollients, and/or lubricants that can be used in the present compositions, either alone or in combination with each other or other ingredients in this disclosure, include Polyglyceryl-4 Caprate, Allantoin, glycine soja (soybean) oil, Panthenol, Vitamin B5, Caprylyl Glycol, C12-15 Alkyl Benzoate, Baobab oil, Camelina oil, and Caster oil.

At least some of the above-described ingredients contain other characteristics that, such as antioxidant characteristics, moisturizing characteristics, cleansing characteristics, preserving characteristics, anti-irritation characteristics, anti-inflammatory characteristics, soothing characteristics, cooling characteristics, antimicrobial characteristics, preservative-boosting characteristics, antibacterial characteristics, and the like, and this disclosure should be understood to include each such characteristic that an ingredient comprises, rather than being limited to those explicitly described herein.

In some embodiments, the pH of the present compositions is substantially equal to (e.g., within 10% of) the average pH of human skin. For example, in some embodiments, the compositions comprise a pH of about 4.5. In other embodiments the compositions comprise a pH of about 4-5. In other embodiments the compositions comprise a pH of about 5-6. In other embodiments, the compositions comprise a pH of about 4-7. The present compositions can also comprise one or more solvents, pH adjustors, and/or acidity adjustors. Examples of solvents, pH adjustors, and/or acidity adjustors that can be used in the present compositions, either alone or in combination with each other or other ingredients in this disclosure, include benzyl alcohol, caprylyl/capryl glucoside, citric acid, Sodium Citrate.

The present disclosure further includes kits. In some embodiments, the kits comprise one or more compositions of the present disclosure, in addition to one or more of a container to dispense the one or more compositions (e.g., a spray bottle, an automatic sprayer) and a substrate/removal material (e.g., toilet tissue/tissue paper (e.g., dry), wet wipes, towels (e.g., paper, cloth, etc.), towelettes, and the like).

EXAMPLES

Tables 1-2 depict various examples of compositions of the present disclosure, each of which can be used as described herein. The volume of each ingredient in a composition, if indicated, is approximate. The volume of water in each mixture is approximately the remainder of the volume of the corresponding bottle size, which is not otherwise occupied by other ingredients. Each of the compositions in Tables 1-2 can be modified (e.g., by varying the types of ingredients, size of bottle, volume of ingredients, and the like) to create further compositions as discussed in detail in this disclosure.

TABLE 1

Examples: Compositions 1-35

| No. | Bottle Size | A | B | C | D | E | F |
|---|---|---|---|---|---|---|---|
| 1 | 15 mL | 2.5 mL Witch Hazel with Alcohol | 1.25 mL Jojoba oil | 0.15 mL Lavender oil (e.g., 3 drops) | 0.15 mL *Eucalyptus* oil (e.g., 3 drops) | Water | |
| 2 | 15 mL | 2.5 mL Witch Hazel with Alcohol | 2.5 mL Jojoba oil | 0.15 mL Lavender oil (e.g., 3 drops) | 0.15 mL *Eucalyptus* oil (e.g., 3 drops) | Water | |
| 3 | 15 mL | 2.5 mL Witch Hazel with Alcohol | 1.25 mL Jojoba oil | 0.2 mL *Eucalyptus* oil (e.g., 4 drops) | Water | | |
| 4 | 15 mL | 2.5 mL Witch Hazel with Alcohol | 1.25 mL Jojoba oil | 0.2 mL Lavender oil (e.g., 4 drops) | Water | | |
| 5 | 15 mL | 2.5 mL Witch Hazel with Alcohol | 1.25 mL Jojoba oil | 0.15 mL Lavender oil (e.g., 3 drops) | Water | | |
| 6 | 15 mL | 3.7 mL Witch Hazel with Alcohol | 1.25 mL Almond oil | 0.15 mL *Eucalyptus* oil (e.g., 3 drops) | Water | | |
| 7 | 30 mL | 7.5 mL Witch Hazel with Alcohol | 5 mL Fractionated Coconut oil | 0.25 mL Castile Soap (e.g., 5 drops) | Water | | |
| 8 | 30 mL | 5 mL Witch | 5 mL | 1.25 mL | Water | | |

TABLE 1-continued

Examples: Compositions 1-35

| No. | Bottle Size | A | B | C | D | E | F |
|---|---|---|---|---|---|---|---|
| | | Hazel with Alcohol | Fractionated Coconut oil | Castile Soap | | | |
| 9 | 30 mL | 5 mL Witch Hazel with Alcohol | 2.5 mL Jojoba oil | 1.25 mL Castile Soap | 0.2 mL *Eucalyptus* oil (e.g., 4 drops) | Water | |
| 10 | 30 mL | 5 mL Witch Hazel with Alcohol | 2.5 mL Fractionated Coconut oil | 0.2 mL *Eucalyptus* oil (e.g., 4 drops) | Water | | |
| 11 | 30 mL | 5 mL Witch Hazel with Alcohol | 2.5 mL Grapeseed oil | 1.25 mL Castile Soap | 0.2 mL Peppermint oil (e.g., 4 drops) | Water | |
| 12 | 30 mL | 5 mL Witch Hazel with Alcohol | 2.5 mL Avocado oil | 0.2 mL Peppermint oil (e.g., 4 drops) | Water | | |
| 13 | 30 mL | 5 mL Witch Hazel with Alcohol | 2.5 mL Avocado oil | 0.2 mL *Geranium* oil (e.g., 4 drops) | Water | | |
| 14 | 30 mL | 5 mL Witch Hazel with Alcohol | 2.5 mL Avocado oil | 0.2 mL Basil oil (e.g., 4 drops) | Water | | |
| 15 | 30 mL | 5 mL Witch Hazel with Alcohol | 1.2 mL Avocado oil | 1.2 mL Almond oil | 0.2 mL Basil oil (e.g., 4 drops) | 0.1 mL *Geranium* oil (e.g., 2 drops) | Water |
| 16 | 30 mL | 5 mL Witch Hazel with Alcohol | 2.5 mL Almond oil | 0.1 mL Basil oil (e.g., 2 drops) | 0.2 mL *Geranium* oil (e.g., 4 drops) | Water | |
| 17 | 30 mL | 5 mL Witch Hazel with Alcohol | 3 mL Fractionated Coconut oil | 2 mL Castile Soap | Water | | |
| 18 | 30 mL | 5 mL Witch Hazel with Alcohol | 2 mL Almond oil | 2 mL Fractionated Coconut oil | 0.15 mL Ylang Ylang oil (e.g., 3 drops) | Water | |
| 19 | 30 mL | 5 mL Witch Hazel with Alcohol | 2 mL Fractionated Coconut oil | 2 mL Grapeseed oil | 0.2 mL Ylang Ylang oil (e.g., 4 drops) | Water | |
| 20 | 30 mL | 5 mL Witch Hazel with Alcohol | 3 mL Avocado oil | 0.05 mL Basil oil (e.g., 1 drops) | 0.15 mL *Geranium* oil (e.g., 3 drops) | Water | |
| 21 | 30 mL | 5 mL Witch Hazel with Alcohol | 2 mL Avocado oil | 2 mL Sesame Seed oil | 0.05 mL Basil oil (e.g., 1 drops) | 0.1 mL *Geranium* oil (e.g., 2 drops) | Water |
| 22 | 30 mL | 3 mL Witch Hazel with Alcohol | 3 mL Almond oil | 3 mL Fractionated Coconut oil | 0.2 mL Ylang Ylang oil (e.g., 4 drops) | Water | |
| 23 | 30 mL | 5 mL Witch Hazel with Alcohol | 3 mL Grapeseed oil | 5 mL *Aloe Vera* oil | Water | | |
| 24 | 30 mL | 5 mL Witch Hazel with Alcohol | 3 mL Apricot oil | 5 mL *Aloe Vera* oil | Water | | |
| 25 | 30 mL | 5 mL Witch Hazel with Alcohol | 4 mL Grapeseed oil | 1 mL Apricot oil | 5 mL *Aloe Vera* oil | Water | |
| 26 | 30 mL | 5 mL Witch Hazel with Alcohol | 3 mL Grapeseed oil | 0.15 mL Peppermint oil (e.g., 3 drops) | Water | | |
| 27 | 30 mL | 6 mL Witch Hazel with Alcohol | 4 mL Grapeseed oil | 5 mL Vegetable Glycerin oil | Water | | |
| 28 | 30 mL | 3 mL Witch Hazel with Alcohol | 3 mL Apricot oil | 3 mL Fractionated Coconut oil | 0.15 mL Ylang Ylang oil (e.g., 3 drops) | Water | |
| 29 | 30 mL | 5 mL Witch Hazel with Alcohol | 3 mL Avocado oil | 0.05 mL Basil oil (e.g., 1 drops) | 0.1 mL *Geranium* oil (e.g., 2 drops) | Water | |
| 30 | 30 mL | 3 mL Witch Hazel with Alcohol | 3 mL Almond oil | 3 mL Fractionated Coconut oil | 0.15 mL Ylang Ylang oil (e.g., 3 drops) | Water | |
| 31 | 30 mL | 5 mL Witch Hazel Distillate | 3 mL Grapeseed oil | 0.15 mL Peppermint oil (e.g., 3 drops) | Water | | |
| 32 | 30 mL | 6 mL Witch Hazel | 4 mL Grapeseed | 5 mL Vegetable | | | |

TABLE 1-continued

Examples: Compositions 1-35

| No. | Bottle Size | A | B | C | D | E | F |
|---|---|---|---|---|---|---|---|
| 33 | 30 mL | 3 mL Witch Hazel Distillate | 3 mL Apricot oil | Glycerin oil 3 mL Fractionated Coconut oil | 0.15 mL Ylang Ylang oil (e.g., 3 drops) | Water | |
| 34 | 30 mL | 5 mL Witch Hazel Distillate | 3 mL Avocado oil | 0.05 mL Basil oil (e.g., 1 drops) | 0.1 mL Geranium oil (e.g., 2 drops) | Water | |
| 35 | 30 mL | 3 mL Witch Hazel Distillate | 3 mL Almond oil | 3 mL Fractionated Coconut oil | 0.15 mL Ylang Ylang oil (e.g., 3 drops) | Water | |

TABLE 2

Examples: Compositions 36-63

| No. | A | B | C | D | E | F | G | H | I |
|---|---|---|---|---|---|---|---|---|---|
| 36 | 10-20% Hamamelis Virginiana (Witch Hazel) | 10-20% Persea gratissima (Avocado) Fruit Oil | 0-1% Ocimum Basilicum (Sweet Basil) Essential Oil | 0-1% Pelargonium graveolens (Geranium) Essential Oil | 0.5-2% Propanediol, Pentylene Glycol, Phenethyl Alcohol | Emulsifier(s) | Remaining percentage water. | | |
| 37 | 10-20% Hamamelis Virginiana (Witch Hazel) | 10-20% Vitis vinifera (Grape) Seed Oil | 0-1% Mentha Piperita (Peppermint) Oil | 0-1% d-alpha Tocopherol (Vitamin E) | 0.5-2% Propanediol, Pentylene Glycol, Phenethyl Alcohol | Emulsifier(s) | Remaining percentage water. | | |
| 38 | 5-15% Hamamelis Virginiana (Witch Hazel) | 5-15% Caprylic/Capric Triglyceride (Fractionated Coconut Oil) | 5-15% Prunus Armeniaca (Apricot) Kernel Oil | 0-1% Cananga odorata (Ylang Ylang) Oil | 0.5-2% Propanediol, Pentylene Glycol, Phenethyl Alcohol | Emulsifier(s) | Remaining percentage water. | | |
| 39 | 10-20% Hamamelis Virginiana (Witch Hazel) | 5-15% Vitis vinifera (Grape) Seed Oil | 10-20% Aloe Barbadensis (Aloe) Leaf Juice | 5-15% Vegetable Glycerin | 0-1% d-alpha Tocopherol (Vitamin E) | 0.5-2% Propanediol, Pentylene Glycol, Phenethyl Alcohol | Emulsifier(s) | Remaining percentage water. | |
| 40 | 5-15% Hamamelis Virginiana (Witch Hazel) | 1-5% Caprylic/Capric Triglyceride (Fractionated Coconut Oil) | 1-5% Prunus Armeniaca (Apricot) Kernel Oil | 5-10% Aloe Barbadensis (Aloe) Leaf Juice | 5-10% Vegetable Glycerin | 0-1% Cananga odorata (Ylang Ylang) Oil | 0.5-2% Propanediol, Pentylene Glycol, Phenethyl Alcohol | Emulsifier(s) | Remaining percentage water. |
| 41 | 5-15% Hamamelis Virginiana (Witch Hazel) | 1-5% Vitis vinifera (Grape) Seed Oil | 5-10% Aloe Barbadensis (Aloe) Leaf Juice | 5-10% Vegetable Glycerin | 0.5-2% Propanediol, Pentylene Glycol, Phenethyl Alcohol | 0-1% d-alpha Tocopherol (Vitamin E) | Emulsifier(s) | Remaining percentage water. | |
| 42 | 5-15% Hamamelis Virginiana (Witch Hazel) | 1-5% Vitis vinifera (Grape) Seed Oil | 5-10% Aloe Barbadensis (Aloe) Leaf Juice | 5-10% Vegetable Glycerin | 0-1% Mentha Piperita (Peppermint) Oil | 0.5-2% Propanediol, Pentylene Glycol, Phenethyl Alcohol | 0-1% d-alpha Tocopherol (Vitamin E) | Emulsifier(s) | Remaining percentage water. |
| 43 | 5-15% Hamamelis Virginiana (Witch Hazel) | 1-5 Persea gratissima (Avocado) Fruit Oil | 5-10% Aloe Barbadensis (Aloe) Leaf Juice | 5-10% Vegetable Glycerin | 0-1% Ocimum Basilicum (Sweet Basil) | 0-1% Pelargonium graveolens (Geranium) | 0.5-2% Propanediol, Pentylene Glycol, Phenethyl Alcohol | Emulsifier(s) | Remaining percentage water. |
| 44 | 3% Carrier Oil 1 | 5-10% Aloe Barbadensis (Aloe) Leaf Juice | 5-10% Vegetable Glycerin | 0.5-2% Preservative 1 | Emulsifier(s) | Remaining percentage water. | | | |

TABLE 2-continued

Examples: Compositions 36-63

| No. | A | B | C | D | E | F | G | H | I |
|---|---|---|---|---|---|---|---|---|---|
| 45 | 3% Carrier Oil 1 | 0.01-0.25% Essential Oil 1 | 5-10% Aloe Barbadensis (Aloe) Leaf Juice | 5-10% Vegetable Glycerin | 0.5-2% Preservative 1 | Emulsifier(s) | Remaining percentage water. | | |
| 46 | 2% Carrier Oil 1 | 2% Carrier Oil 2 | 5-10% Aloe Barbadensis (Aloe) Leaf Juice | 5-10% Vegetable Glycerin | 0.5-2% Preservative 1 | Emulsifier(s) | Remaining percentage water. | | |
| 47 | 2% Carrier Oil 1 | 2% Carrier Oil 2 | 0.01-0.25% Essential Oil 1 | 5-10% Aloe Barbadensis (Aloe) Leaf Juice | 5-10% Vegetable Glycerin | 0.5-2% Preservative 1 | Emulsifier(s) | Remaining percentage water. | |
| 48 | 5% Carrier Oil 1 | 5-10% Aloe Barbadensis (Aloe) Leaf Juice | 5-10% Vegetable Glycerin | 0.5-2% Preservative 1 | Emulsifier(s) | Remaining percentage water. | | | |
| 49 | 5% Carrier Oil 1 | 0.01-0.25% Essential Oil 1 | 5-10% Aloe Barbadensis (Aloe) Leaf Juice | 5-10% Vegetable Glycerin | 0.5-2% Preservative 1 | Emulsifier(s) | Remaining percentage water. | | |
| 50 | 3% Carrier Oil 1 | 3% Carrier Oil 2 | 5-10% Aloe Barbadensis (Aloe) Leaf Juice | 5-10% Vegetable Glycerin | 0.5-2% Preservative 1 | Emulsifier(s) | Remaining percentage water. | | |
| 51 | 3% Carrier Oil 1 | 3% Carrier Oil 2 | 0.01-0.25% Essential Oil 1 | 5-10% Aloe Barbadensis (Aloe) Leaf Juice | 5-10% Vegetable Glycerin | 0.5-2% Preservative 1 | Emulsifier(s) | Remaining percentage water. | |
| 52 | 10% Carrier Oil 1 | 5-10% Aloe Barbadensis (Aloe) Leaf Juice | 5-10% Vegetable Glycerin | 0.5-2% Preservative 1 | Emulsifier(s) | Remaining percentage water. | | | |
| 53 | 10% Carrier Oil 1 | 0.01-0.25% Essential Oil 1 | 5-10% Aloe Barbadensis (Aloe) Leaf Juice | 5-10% Vegetable Glycerin | 0.5-2% Preservative 1 | Emulsifier(s) | Remaining percentage water. | | |
| 54 | 5% Carrier Oil 1 | 5% Carrier Oil 2 | 5-10% Aloe Barbadensis (Aloe) Leaf Juice | 5-10% Vegetable Glycerin | 0.5-2% Preservative 1 | Emulsifier(s) | Remaining percentage water. | | |
| 55 | 5% Carrier Oil 1 | 5% Carrier Oil 2 | 0.01-0.25% Essential Oil 1 | 5-10% Aloe Barbadensis (Aloe) Leaf Juice | 5-10% Vegetable Glycerin | 0.5-2% Preservative 1 | Emulsifier(s) | Remaining percentage water. | |
| 56 | 10% Carrier Oil 1 | 0.5-2% Preservative 1 | Emulsifier(s) | Remaining percentage water. | | | | | |
| 57 | 10% Carrier Oil 1 | 0.01-0.25% Essential Oil 1 | 0.5-2% Preservative 1 | Emulsifier(s) | Remaining percentage water. | | | | |
| 58 | 5% Carrier Oil 1 | 5% Carrier Oil 2 | 0.5-2% Preservative 1 | Emulsifier(s) | Remaining percentage water. | | | | |
| 59 | 5% Carrier Oil 1 | 5% Carrier Oil 2 | 0.01-0.25% Essential Oil 1 | 0.5-2% Preservative 1 | Emulsifier(s) | Remaining percentage water. | | | |
| 60 | 15% Carrier Oil 1 | 0.5-2% Preservative 1 | Emulsifier(s) | Remaining percentage water. | | | | | |
| 61 | 15% Carrier Oil 1 | 0.01-0.25% Essential Oil 1 | 0.5-2% Preservative 1 | Emulsifier(s) | Remaining percentage water. | | | | |
| 62 | 7% Carrier Oil 1 | 7% Carrier Oil 2 | 0.5-2% Preservative 1 | Emulsifier(s) | Remaining percentage water. | | | | |

TABLE 2-continued

Examples: Compositions 36-63

| No. | A | B | C | D | E | F | G | H | I |
|---|---|---|---|---|---|---|---|---|---|
| 63 | 7% Carrier Oil 1 | 5% Carrier Oil 2 | 0.01-0.25% Essential Oil 1 | 0.5-2% Preservative 1 | Emulsifier(s) | Remaining percentage water. | | | |

The above specification and examples provide a complete description of the ingredients, compositions, and use of exemplary embodiments. Although certain embodiments have been described above with a certain degree of particularity, or with reference to one or more individual embodiments, those skilled in the art could make numerous alterations to the disclosed embodiments without departing from the scope of this invention. The various illustrative embodiments of the present compositions and methods are not intended to be limited to the particular forms disclosed. Rather, they include all modifications and alternatives falling within the scope of the claims, and embodiments other than the ones shown may include some or all of the features of the disclosed embodiments. For example, one or more ingredients may be added to compositions for one or more other ingredients, or one or more ingredients may be substituted for one or more other ingredients. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A composition, comprising:
    water at about 50% or greater by volume of the composition;
    one or more surfactant agents;
    one or more naturally occurring or naturally derived cleansing agents at about 5% or greater by volume of the composition; and
    at least one preservative at about 0.5-2% by volume of the composition;
    where the composition is configured to cleanse the skin of a subject;
    where the composition comprises a viscosity of less than or equal to about 100 millipascal-seconds at room temperature;
    where at least 95% of the ingredients in the composition are naturally occurring or naturally derived;
    where at least one ingredient in the composition is configured to at least one of remove, reduce, and prevent microbial or bacteria growth;
    where the composition is substantially liquid such that it can be atomized by a spraying device without creating a blockage in the spraying device that substantially prevents exit of the composition; and
    where the composition is a rinse-free composition.

2. The composition of claim 1, where the composition comprises at least one of aloe vera leaf juice and aloe vera oil.

3. The composition of claim 1, where a viscosity of the composition comprises less than or equal to approximately 20 millipascal-seconds at room temperature.

4. The composition of claim 1, where each of the ingredients in the composition are naturally occurring or naturally derived.

5. The composition of claim 1, where one of the one or more naturally occurring or naturally derived cleansing agents comprises witch hazel.

6. The composition of claim 1, where the at least one ingredient in the composition that is configured to at least one of remove, reduce, and prevent microbial or bacteria growth is a different ingredient than the one or more naturally occurring or naturally derived cleansing agents.

7. The composition of claim 1, where the at least one ingredient in the composition that is configured to at least one of remove, reduce, and prevent microbial or bacteria growth prevents microbial or bacteria growth.

8. The composition of claim 1, where the at least one ingredient in the composition that is configured to at least one of remove, reduce, and prevent microbial or bacteria growth is naturally occurring or naturally derived.

9. The composition of claim 8, where the at least one ingredient in the composition that is configured to at least one of remove, reduce, and prevent microbial or bacteria growth further comprises surfactant properties and solubilizer properties.

10. A composition, comprising:
    water at about 50% or greater by volume of the composition;
    one or more surfactant agents; and
    at least one ingredient configured to at least one of remove, reduce, and prevent microbial or bacteria growth;
    where the composition is configured to cleanse the skin of a subject;
    where the composition comprises a viscosity of less than or equal to about 100 millipascal-seconds at room temperature;
    where the at least one ingredient in the composition that is configured to at least one of remove, reduce, and prevent microbial or bacteria growth is naturally occurring or naturally derived;
    where the composition is substantially liquid such that it can be atomized by a spraying device without creating a blockage in the spraying device that substantially prevents exit of the composition; and
    where the composition is a rinse-free composition.

11. The composition of claim 10, where the composition further comprises at least one oil at 1% or greater by volume of the composition.

12. The composition of claim 10, where each ingredient in the composition is naturally occurring or naturally derived.

13. The composition of claim 10, further comprising:
    at least one preservative;

where the at least one preservative is naturally occurring or naturally derived.

14. The composition of claim 10, further comprising:
at least one cleansing agent at 3% or greater by volume of the composition;
where the at least one cleansing agent is different from the at least one ingredient configured to at least one of remove, reduce, and prevent microbial or bacteria growth.

15. The composition of claim 10, where the at least one ingredient configured to at least one of remove, reduce, and prevent microbial or bacteria growth further comprises surfactant properties and preservative-boosting properties.

16. The composition of claim 10, further comprising:
at least one lubricant.

17. The composition of claim 10, where the composition further comprises:
at least one fragrance that is naturally occurring or naturally derived.

18. The composition of claim 10, where the at least one ingredient in the composition that is configured to at least one of remove, reduce, and prevent microbial or bacteria growth prevents microbial or bacteria growth.

19. A method, comprising:
preparing a composition comprising:
water at about 50% or greater by volume of the composition;
one or more surfactant agents; and
at least one ingredient configured to at least one of remove, reduce, and prevent microbial or bacteria growth;
where the composition is configured to cleanse the skin of a subject;
where the composition comprises a viscosity of less than or equal to about 100 millipascal-seconds at room temperature;
where the at least one ingredient in the composition that is configured to at least one of remove, reduce, and prevent microbial or bacteria growth is naturally occurring or naturally derived;
where the composition is substantially liquid such that it can be atomized by a spraying device without creating a blockage in the spraying device that substantially prevents exit of the composition; and
where the composition is a rinse-free composition;
disposing the composition in a spray bottle; and
spraying the composition.

20. The method of claim 19, where each ingredient in the composition is naturally occurring or naturally derived.

* * * * *